United States Patent
Rupert

[11] Patent Number: 5,413,936
[45] Date of Patent: May 9, 1995

[54] ROTARY BIOFILTER

[76] Inventor: Richard Rupert, 1615 E. Monte Cristo Ave., Phoenix, Ariz. 85022

[21] Appl. No.: 157,978

[22] Filed: Nov. 29, 1993

[51] Int. Cl.$^6$ .................... C12M 1/16; C12M 1/10; C12M 1/04; C14C 1/00
[52] U.S. Cl. .................... 435/299; 435/312; 435/313; 435/266; 55/261; 55/528
[58] Field of Search .............. 435/312, 313, 314, 299, 435/266; 55/261, 528

[56] References Cited

U.S. PATENT DOCUMENTS

| | | | |
|---|---|---|---|
| 4,734,111 | 3/1988 | Hoffmann et al. | 55/97 |
| 4,786,297 | 11/1988 | Gethke et al. | 55/259 |
| 4,849,360 | 7/1989 | Norris et al. | 435/264 |
| 4,999,302 | 3/1991 | Kahler et al. | 435/266 |
| 5,056,960 | 10/1991 | Marienfeld | 405/270 |
| 5,139,953 | 8/1992 | Honda et al. | 435/312 |
| 5,159,694 | 10/1992 | Overath et al. | 435/288 |

OTHER PUBLICATIONS

"Biofiltration: An Innovative Air Pollution Control Technology for VOC Emissions", Leson and Winer, J. Air Waste Manage. Assoc., vol. 41, No. 8 (Aug. 1991) pp. 1045-1053.
"Removal of Volatile Aliphatic Hydrocarbons in a Soil Bioreactor"; Kampbell et al., JAPCA, vol. 37, No. 10 (Oct. 1987) pp. 1236-1240.

Primary Examiner—Michael G. Wityshyn
Assistant Examiner—Timothy J. Reardon
Attorney, Agent, or Firm—Cahill, Sutton & Thomas

[57] ABSTRACT

A cylindrical vessel having a horizontal, longitudinal axis of rotation is filled with biofilter material and receives gases through a perforated dispersion pipe located along the axis. Humidified gases pass through the biologically active filter material where the gases are converted into elemental gases, carbon dioxide, biomass, or water. The vessel is lined with geotextile material which acts as a collection plenum for the gases which flow radially outward to the lining. Collection pipes located at regular intervals between the lining and the vessel conduct the gases to a manifold, also located on the axis. The vessel is rotated periodically, e.g. weekly, for several rotations in order to mix the filter material, break up any compacted material, and collapse any fissures.

13 Claims, 2 Drawing Sheets

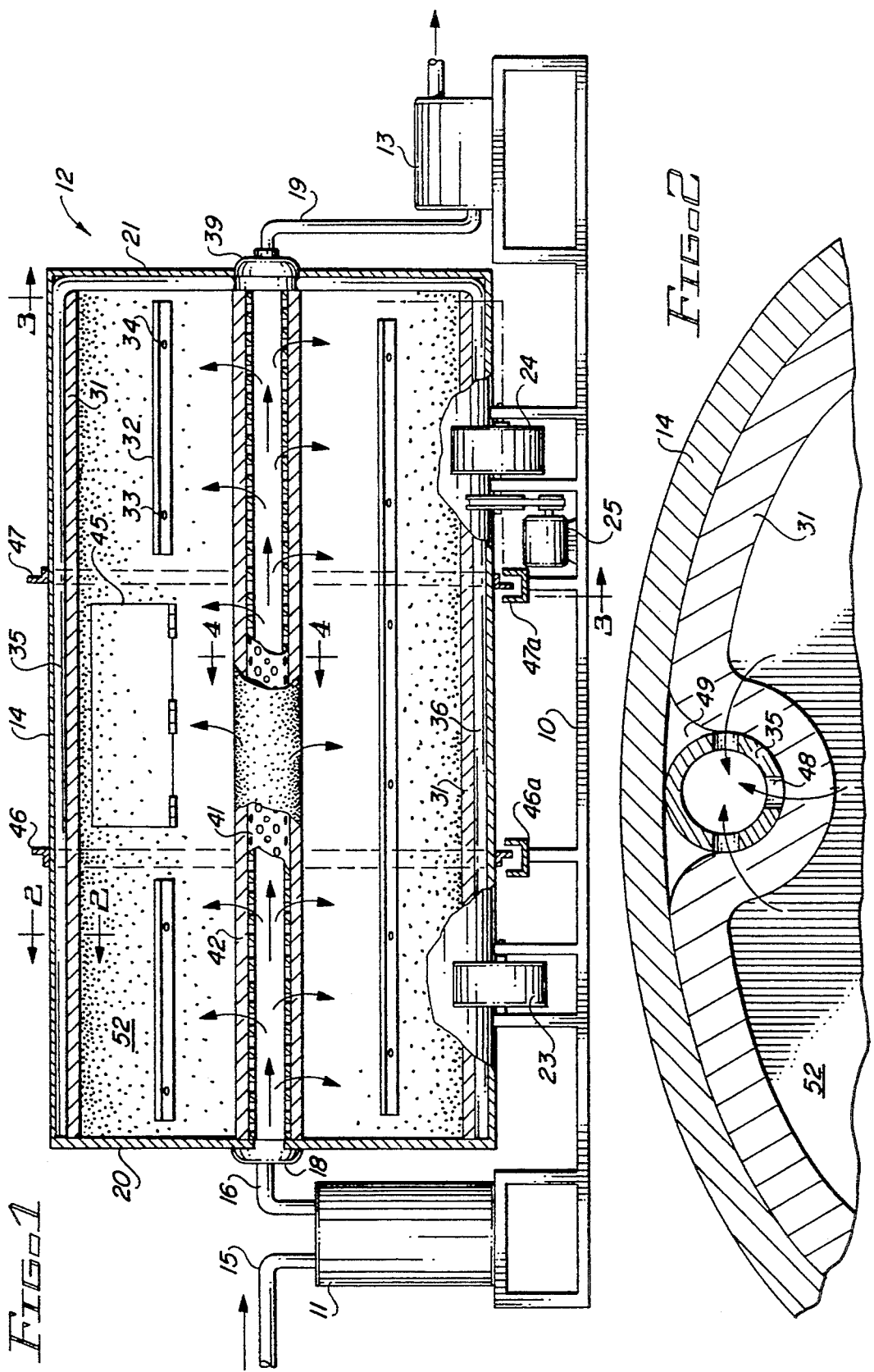

ROTARY BIOFILTER

BACKGROUND

This invention relates to bioremediation of contaminated vapors and, in particular, to a rotary biofilter for removing and destroying volatile organic compounds and inorganic air toxins.

Microbes, e.g. bacteria, fungi, protozoa, and yeast, are the oldest forms of life but, until recently, have been little used by man except for making bread, wine, and cheese. Only within the last twenty years have microbes been used for recycling industrial waste, principally in Europe and Japan.

Bioremediation has been used for eliminating odors and pollutants from the by-products of industry, e.g. food processing and waste water treatment. Recycling depends upon the discovery that, among the millions of omnipresent microbes, some microbes can digest waste, even substances such as cyanides that are toxic to human beings and to most other life forms.

A typical biofilter includes a filter bed, a pump for blowing untreated air or gases through the filter bed, and a humidifier connected between the pump and the filter. The humidifier is needed to prevent the gases from drying the filter bed. The filter bed is at least one meter deep and can be soil, compost, or an inorganic material having a large surface area such as sand, porous clay, or small polystyrene spheres.

The operation of a biofilter is not completely understood but is generally believed to take place in a thin film of water, known as a "biofilm," surrounding each particle in the filter bed. Gases dissolve into the film and microbes in the film use the dissolved gases as sources of carbon and energy, metabolizing or converting the gases into non-toxic by-products, such as elemental gases or carbon dioxide.

Industrial uses of biofilters typically involve large volumes of gases having a low concentration of organic pollutants, e.g., less than 1,000 parts per million. Biofiltration for pollution control can involve much higher concentrations of gases and gases that are slowly biodegradable. For example, alcohols, ethers, and some of the more common monocyclic aromatics degrade quickly. Highly chlorinated organics tend to degrade much more slowly.

The size of the biofilter depends on the volume of gases, their concentration, and transit time. Transit time is the time for the gases to flow from a supply pipe through the bulk of the biofilter to an outer surface. For complete conversion of the gases, the transit time must exceed the time required for the gases biodegrade.

In a typical application, the filter bed is large, occupying several thousand square feet of land or floor space, and is immovable. In addition to the sheer size of typical biofilters, there are two problems relating to the filter material. One problem is compaction of the filter material and the other problem is fissuring in the filter material. While seemingly opposite, both problems can occur simultaneously.

The filter bed is preferably a homogeneous, porous material having a large surface area. The water film adds weight to the material, softening it, and gravity and decomposition of organic matter causes the material to compact. As the filter compacts, it becomes less efficient at treating the gases and less permeable to the gases, i.e. the pressure drop across the filter increases and the flow of gases through the filter decreases. Compaction can also cause inhomogeneities in the filter bed because the microbes are cut off from their food source and die, decreasing the capacity of the biofilter. Stirring or raking the filter bed may not be sufficient to assure homogeneity if a die-off occurred. Fissures, on the other hand, are favored paths taken by the gases without coming into intimate contact with the biofilm. The result is untreated gases escaping from the filter. Thus, maintenance of a filter bed is a continuing problem.

Large scale industrial operations are not the only applications for biofilters. A frequently occurring example is the remediation of soils contaminated with volatile organic compounds, such as gasoline, from leaking underground storage tanks. In theory, some soils will recover on their own if the leaking is stopped but recovery can take a long time and the leakage plume may reach underground water supplies in the meantime.

Corrective action requires reducing the concentration of the pollutants as quickly as possible. Typical remedial operations include extracting the volatile compounds through a system of pipes in the ground for withdrawing the compounds from the ground and pumping the compounds into an incinerator. There are several disadvantages to incineration. The energy required for burning the contaminated vapors can be expensive, as can the maintenance of the incinerator. Also, combustion byproducts may themselves pose environmental and health risks.

For these reasons, bioremediation is particularly appealing. Capital and operating costs are lower than for other air pollution control technologies and the only emissions or by-products of a properly run biofilter are carbon dioxide, water, and biomass. However, until now, bioremediation systems typically require large areas and have not been particularly suited to temporary location at sites of small spills or leaks such as at gas stations.

In view of the foregoing, it is therefore an object of the invention to provide a rotary biofilter for converting waste or pollutants into harmless by-products.

Another object of the invention is to provide a biofilter in which compaction of the filter bed is minimized.

A further object of the invention is to provide a biofilter in which fissures in the filter bed are minimized.

Another object of the invention is to provide a biofilter which can be transported to the site of a small spill or leak of waste or contamination.

A further object of the invention is to provide a biofilter having reduced pressure drop.

Another object of the invention is to provide a biofilter requiring little maintenance.

SUMMARY OF THE INVENTION

The foregoing objects are achieved in the invention in which a cylindrical vessel having a horizontal, longitudinal axis is filled with biofilter material and receives gases through an axial dispersion pipe. Humidified gases pass radially outward through the biologically active filter material where the gases are converted into elemental gases, carbon dioxide, biomass, or water. The vessel and the dispersion pipe are lined with geotextile material which acts as a plenum for the gases. Collection pipes located at regular intervals between the lining of the vessel and the cylindrical outer wall of the vessel conduct the gases to a manifold through which they exit the vessel. In one embodiment of the invention, the filter material includes well composted horse manure blended with mulch (wood chips) and diatomaceous earth. The vessel is rotated periodically, e.g. weekly, for several rotations in order to mix the filter material, break up any compacted material, and collapse any fissures. This action sustains a homogeneous mixture which promotes healthy microbe growth and maintains maximum porosity and permeability.

BRIEF DESCRIPTION OF THE DRAWINGS

A more complete understanding of the invention can be obtained by considering the following detailed description in conjunction with the accompanying drawings, in which:

FIG. 1 is a longitudinal cross-section of a rotary biofilter constructed in accordance with the invention;

FIG. 2 is detail showing the location of a collection pipe;

DETAILED DESCRIPTION OF THE INVENTION

Figure 3:
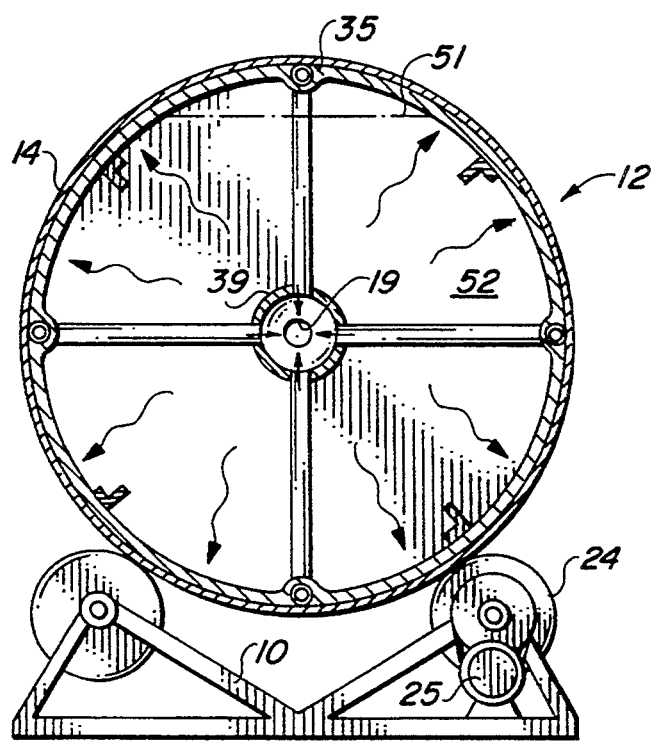
FIG. 3 is a transverse cross-section of a rotary biofilter constructed in accordance with the invention.

FIG. 1 illustrates a biofilter constructed in accordance with a preferred embodiment of the invention. The basic components of the biofilter include frame 10 supporting humidifier 11, rotatable vessel 12, and pump 13. Humidifier 11 includes supply pipe 15 connected to a source of gases to be treated. Pipe 16 connects humidifier 11 to vessel 12 through rotating joint 18. Pump 13 exhausts gases from vessel 12 through pipe 19. As understood by those of skill in the art, the filter material should not become dried out as the gases are drawn through vessel 12 by pump 13. Humidifier 11 preferably maintains a moisture content of from 40%-60% by weight in the filter material.

Rotatable vessel 12 includes cylindrical outer wall 14 and closed ends 20 and 21. Vessel 12 is supported on several wheels, such as wheels 23 and 24, one of which is driven by motor 25 for rotating the vessel about a substantially horizontal longitudinal axis. Thrust bearings 46 and 47 prevent longitudinal motion of the vessel as it is rotated and provide radial reinforcement around hatch 45. Thrust bearings 46 and 47 are preferably in the form of angle iron welded to the outside of vessel 12 along a circumference of vessel 12 on either side of hatch 45. An outwardly extending flange of bearing 46 fits within U-shaped bracket 46a and an outwardly extending flange of bearing 47 fits within U-shaped bracket 47a. Brackets 46a and 47a are welded to frame 10 and include suitable bearing surfaces for engaging the flange of the angle iron.

Liner 31 is adjacent the inside of outer wall 14 and is preferably held in place by sections of angle iron, such as angle iron 32 fastened to studs 33 and 34 and extending lengthwise inside vessel 12. Located between liner 31 and outer wall 14 of vessel 12 are perforated pipes 35 and 36. These pipes are attached to pipe 19 through manifold 39 and collect the treated gases emanating from the filter material. Perforated pipe 41 extends along the longitudinal axis of vessel 12 and is surrounded by sleeve 42. Perforated pipe 41 also strengthens vessel 12 by reinforcing ends 20 and 21.

Liner 31 and sleeve 42 can be any permeable material and are preferably geotextile material. Geotextile material is a self-supporting liner made from a plastic mesh or web which is covered on both sides with a wool-like synthetic material. This material is commercially available in rolls fourteen feet wide and one hundred feet long from Gundle Lining Systems, Inc of Houston, Tex., under the trademark "Fabri-Net ®". Geotextile material is typically used in landfills as a substitute for sand since a layer of geo-textile material approximately one-half inch thick has the permeability of six to seven inches of washed, fine grain sand.

The geotextile materials serves two functions in a biofilter constructed in accordance with the invention. A first function is to prevent the filter material from entering the holes in the perforated pipes and plugging the pipes. A second function is to act as a plenum for supplying gases to the filter material or for collecting treated gas. This construction provides a particularly uniform distribution of gases through the filter material.

FIG. 2 is a cross-section along lines 2—2 in FIG. 1 showing the location and operation of one of the collection pipes. Pipe 35 is located between outer wall 14 and liner 31 and includes a plurality of holes, such as hole 48, around its perimeter and along its length. Gas from filter material 52 flows through liner 31 and through one of the holes in pipe 35 to the interior of pipe 35. Liner 31 and void 49 act as a plenum for collecting gases from filter material 52 and the gases can flow longitudinally as well as radially through the liner to a hole in a collecting pipe. This provides a uniform collection of gases and efficient operation of the filter.

In FIG. 1, hatch 45 provides a convenient access for loading or unloading filter material in vessel 12. The filter material is preferably a fine grain compost and, in one embodiment of the invention, includes well-composted horse manure blended with a mulch of wood chips and diatomaceous earth. Permeability of the filter material can be improved by blending a fine grain sand into the compost. The ratio of the sand to compost depends on the grade of compost used; the finer the compost, the more sand is desirable. Assuming a fine grain compost material is used, the sand forms ten percent or less of the mixture. The mulch aids the filter material by acting as a moisture reservoir and as an absorptive medium. The diatomaceous earth enhances permeability, increases the concentration of microbes within the filter, protects the microbes from damaging fluid movement, and helps protect the beneficial microbes from destructive microbes within the biofilter.

As known in the art, the filter material should have a pH between 7 and 8. In order to assure that this condition is obtained, limestone chips can be added to prevent the pH from going below 7. The limestone chips are relatively inactive until the pH drops below 7, at which point the limestone reacts with the acids to form carbon dioxide and a salt.

FIG. 3 illustrates the operation of the invention. Vessel 12 is filled as much as possible without compacting the material, e.g. to level 51. After filling, vessel 12 is rotated several times to assure a homogeneous mixture of the filter material. The mixing action obtained from rolling vessel 12 is particularly effective due to the milling action of the material as it is rotated and falls on itself within vessel 12. In addition, the angle iron holding liner 31 in place aids the mixing action by extending into the filter material and causing locally turbulent movement of the filter material.

Gases supplied through the axial dispersion pipe flow radially outward through filter material 52 toward liner 31. As the gases travel toward liner 31 they encounter substantially more filter material than in the prior art, i.e. the concentration of the gases per volume of filter material is inversely proportional to the square of the distance from the axis of the cylinder.

This is quite different from biofilters of the prior art in which a rectangular container includes the entire bottom surface of the container as a plenum and the gases flow upwardly through the filter material. In biofilters of the prior art, the gases travel through a volume of filter material that increases linearly with distance from the supply plenum. In the rotary biofilter illustrated in FIG. 3, filter material 52 completely surrounds pipe 41 and sleeve 42 and the volume of filter material increases with the square of the distance from pipe 41. This greatly increases the available filter material without increasing the distance through which the gases must travel.

It is generally accepted that the preferred thickness for filter material is approximately one meter. The configuration illustrated in FIG. 3 provides a significantly greater volume of filter material while maintaining a distance of approximately one meter from the supply to the exhaust system. In addition, since the gases enter along the central axis of the vessel and travel outwardly, the velocity of the gases is greatest and the contact time is shortest near the perforated pipe where the gas concentration is the highest. Conversely, near the cylindrical outer surface of the filter material, the gas velocity is much lower, the contact time is much greater, and there is much more filter material available for absorbing contaminants. Thus, the rotary biofilter provides a much more uniform concentration of contaminants through the filter and a more uniform population of microbes. By supplying gases to the central portion of the volume of filter material and withdrawing by-products at the outer surface of the filter material, the homogeneity of the filter material is further enhanced.

Figure 4:
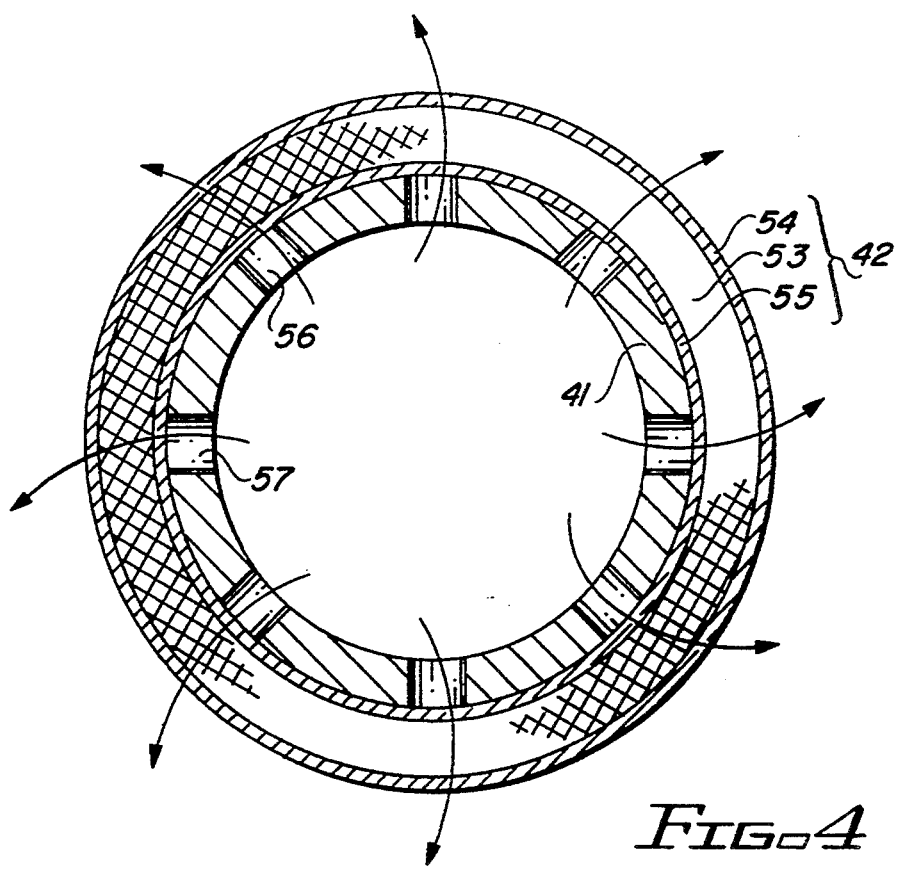
FIG. 4 is a cross-section of the axial dispersion pipe.

FIG. 4 is a cross-section along lines 4—4 in FIG. 1 showing the construction of sleeve 42 and the operation of the axial dispersion pipe. Pipe 41 includes a plurality of holes, such as holes 56 and 57, around its perimeter and along its length. Because of the pressure drop along the length of pipe 41, the size and/or distribution of the holes is not uniform but is inversely related to the distance from the source of gases, i.e. there are fewer and-/or smaller holes nearer the source.

Sleeve 42 includes plastic web 53 sandwiched between outer layer 54 and inner layer 55. Layers 54 and 55 are a synthetic, wool-like material looking something like felt but much more porous. Humidified gases within pipe 41 flow through holes 56 and 57 and through sleeve 42 into the filter material. Sleeve 42 prevents filter material from working its way through the holes into pipe 41 and permits the gases to flow longitudinally and radially, thereby providing a very uniform dispersion of gases into the interior volume of the filter material.

Operation and maintenance of the rotary biofilter is greatly simplified compared to the maintenance required in systems of the prior art. In addition to occasionally, e.g. weekly, rotating the vessel, one need only perform routine lubrication and occasionally add filter material. Depending upon the moisture content of the filter material, accumulated liquid might have to be drained occasionally.

Vessel 12 preferably has a diameter of approximately two meters and a length determined by the volume of gas to be processed. In one embodiment of the invention, vessel 12 has a length of thirty feet and can be mounted on a trailer for towing to a cleanup site. Other embodiments of the invention can have other dimensions, as determined by the particular filter material chosen, the nature of the gases being processed, and other factors known to those of skill in the art for sizing a filter to a particular task.

The invention thus provides an improved filter for removing waste or pollutants from contaminated soil and converting the gases into harmless by-products. By virtue of the rotary action of the vessel, maintenance of the bed is greatly simplified, homogeneity is assured, compaction of the filter material is minimized, and fissures in the filter material are eliminated.

Having thus described the invention, it will be apparent to those of skill in the art that various modifications can be made within the scope of the invention. For example, although a geotextile material is preferred as a liner for the vessel and as a sleeve for the perforated, axial dispersion pipe, other materials can be substituted. Instead of feeding the axial dispersion pipe from an end, an inner pipe can be used, half the length of the axial dispersion pipe, to introduce gases at the middle of the axial dispersion pipe, thereby reducing the pressure drop along the dispersion pipe by half but making the plumbing slightly more complicated. Various types of blowers or vacuum devices can ! be used to pump the gases through the filter. The pump is located downstream of the filter in FIG. 1. This arrangement used in high ambient temperature conditions to avoid excessive heating, and drying, of the gases due to compression within the pump. In cold climates, the pump can be placed upstream of the humidifier to heat the contaminated gases.

I claim:

1. A rotary biofilter for removing and destroying volatile organic compounds and inorganic toxins from gases, said biofilter comprising:
   (a) a vessel having
      (i) a cylindrical outer wall defining a horizontal, longitudinal axis of rotation;
      (ii) a first, closed end and a second, closed end;
      (iii) an axial dispersion pipe positioned approximately along said axis and having an open end extending to the exterior of the vessel through said first closed end for supplying said gases to the interior of said vessel,
      (iv) a porous lining about the interior of said cylindrical outer wall, and
      (v) perforated collection pipes located between said lining and said outer wall, said collection pipes being coupled through said second closed end for removing treated gases from said vessel;
   (b) a quantity of biofilter material substantially filling the volume of said vessel between said axial dispersion pipe and said lining;
   (c) a humidifier connected to the open end of said axial dispersion pipe for increasing the moisture content of gases entering said vessel; and
   (d) a pump exterior to said vessel and coupled to either said dispersion pipe or said collection pipes for forcing gases into said dispersion pipe, through said biofilter material, and into said collection pipes.

2. The biofilter as set forth in claim 1 wherein said pump is coupled to said collection pipes for drawing said gases out of said filter.

3. The biofilter as set forth in claim 1 wherein said pump is coupled to the open end of said axial dispersion pipe for forcing said gases into said filter.

4. The biofilter as set forth in claim 1 and further comprising:
   a motor for rotating said biofilter.

5. The biofilter as set forth in claim 1 wherein said pump is located upstream of said vessel.

6. The biofilter as set forth in claim 5 wherein said pump is located upstream of said humidifier.

7. The biofilter as set forth in claim 1 wherein said pump is located downstream from said vessel.

8. A container for biofilter material, said container comprising:
   a hollow vessel having a cylindrical outer wall and substantially closed ends;
   a liner of porous material adjacent the inside of said cylindrical outer wall, said liner collecting gases passing through said material;
   a perforated dispersion pipe within said vessel and having an end extending to the exterior of the vessel through one of the closed ends of said vessel, said dispersion pipe supplying gases to said container for treatment;
   a sleeve of porous material around said perforated dispersion pipe within said vessel, said sleeve preventing said biofilter material from entering said dispersion pipe; and
   a plurality of perforated collection pipes located between said liner and said cylindrical outer wall, said collection pipes being coupled through another of said closed ends for removing treated gases from said vessel was inserted.

9. The container as set forth in claim 8 wherein said collection pipes are uniformly distributed about said outer wall.

10. The container as set forth in claim 9 wherein said vessel has a longitudinal axis of rotation and said dispersion pipe is located along said axis.

11. The container as set forth in claim 8 wherein said vessel has a longitudinal axis of rotation and said dispersion pipe is located along said axis.

12. The container as set forth in claim 8 wherein said cylindrical outer wall includes a hatch for access to the interior of said vessel.

13. The container as set forth in claim 8 wherein said porous material is geotextile material.

* * * * *